United States Patent
Friedman et al.

(10) Patent No.: US 9,279,158 B2
(45) Date of Patent: Mar. 8, 2016

(54) COMPOSITIONS AND METHODS USEFUL FOR THE TREATMENT AND DIAGNOSIS OF INFLAMMATORY BOWEL DISEASE

(71) Applicant: The Children's Hospital of Philadelphia, Philadelphia, PA (US)

(72) Inventors: Joshua R. Friedman, Ardmore, PA (US); Adam Zahm, Philadelphia, PA (US); Meena Thayu, Bryn Mawr, PA (US); Nicholas Hand, Philadelphia, PA (US); Edwin deZoeten, Denver, CO (US)

(73) Assignee: The Children's Hospital of Philadelphia, Philadelphia, PA (US)

(*) Notice: Subject to any disclaimer, the term of this patent is extended or adjusted under 35 U.S.C. 154(b) by 0 days.

(21) Appl. No.: 13/851,623

(22) Filed: Mar. 27, 2013

(65) Prior Publication Data

US 2013/0225440 A1 Aug. 29, 2013

Related U.S. Application Data

(63) Continuation of application No. PCT/US2011/053417, filed on Sep. 27, 2011.

(60) Provisional application No. 61/386,754, filed on Sep. 27, 2010.

(51) Int. Cl.
*C07H 21/04* (2006.01)
*C12Q 1/68* (2006.01)
*C07H 21/02* (2006.01)

(52) U.S. Cl.
CPC ............ *C12Q 1/6886* (2013.01); *C12Q 1/6883* (2013.01); *C12Q 2600/106* (2013.01); *C12Q 2600/136* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2007/0161004 A1* 7/2007 Brown et al. ............. 435/6
2008/0182245 A1 7/2008 Brown et al.
2011/0117111 A1 5/2011 Kwon et al.

FOREIGN PATENT DOCUMENTS

WO 2009/120877 A2 * 10/2009 ............ C12Q 1/68

OTHER PUBLICATIONS

Ahmed et al., "Diagnostic MicroRNA Markers for Screening Sporadic Human Colon Cancer and Active Ulcerative Colitis in Stool and Tissue" 6 Cancer Genomics & Proteomics 281-296 (2009).*
Sharbati-Tehrani et al., "Concatameric cloning of porcine microRNA molecules after assembly PCR" 375 Biochemical and Biophysical Research Communications 484-489 (2008).*
Taylor et al., "MicroRNA signatures of tumor-dervied exosomes as diagnostic biomarkers of ovarian cancer" 110 Gynecologic Oncology 13-21 (2008).*
Wu et al. "Identification of MicroRNAs associated with ileal and colonic Crohn's disease." Inflamm Bowl Dis. Jun. 2, 2010;16:1729-1738.
Okubo et al. "Associated study of common genetic variants in pre-microRNAs in patients with ulcerative colitis." J Clin Immunol. Sep. 17, 2010;31:69-73.
Dalal et al., "The rold of microRNA in inflammatory bowel disease." Gastroenterology & Heptatology. Nov. 2010;6 (11):714-722.
Feng Wu et al., "Peripheral blood MicroRNAs distinguish active ulcerative colitis and Crohn's disease," Inflammatory Bowel Diseases (2010) 17:241-250.
Feng Wu et al., "MicroRNAs are differentially expressed in ulcerative colitis and alter expression of macrophage inflammatory peptide-2a," Gastroenterology (2008) 135:1624-1635.
Adam M Zahm et al., "Circulating MicroRNA is a biomarker of pediatric Crohn disease," Journal of Pediatric Gastroenterology and Nutrition (2011) 53:26-33.
Extended European Search Report from European Patent Application No. 11831280.0, dated Jan. 31, 2014.

* cited by examiner

*Primary Examiner* — Nancy J Leith
(74) *Attorney, Agent, or Firm* — Kathleen D. Rigaut; Dann, Dorfman, Herrell & Skillman

(57) ABSTRACT

Compositions and methods useful for the diagnosis and treatment of IBD including Crohn's disease are disclosed.

6 Claims, 6 Drawing Sheets

COMPOSITIONS AND METHODS USEFUL FOR THE TREATMENT AND DIAGNOSIS OF INFLAMMATORY BOWEL DISEASE

This application is being filed under 35 U.S.C. §365 and claims priority to PCT/US011/53417 filed Sep. 27, 2011 which in turn claims priority to U.S. Provisional Application 61/386,754 filed Sep. 27, 2010, each of the foregoing applications being incorporated by reference herein.

FIELD OF THE INVENTION

This invention relates to the fields of inflammation and inflammatory bowel disease (IBD). More specifically, the invention provides compositions and methods for the diagnosis and treatment of inflammatory diseases and disorders, and more particularly, Inflammatory Bowel disease (IBD) including Crohn's disease (CD) and Ulcerative colitis (UC), via the detection and manipulation of microRNA (miRNA) levels.

BACKGROUND OF THE INVENTION

Several publications and patent documents are cited throughout the specification in order to describe the state of the art to which this invention pertains. Each of these citations is incorporated by reference herein as though set forth in full.

The diagnosis of inflammatory bowel disease (IBD) is often achieved only months or years after the onset of symptoms. Several serological indicators of IBD have been identified; in general, they are antibodies directed against antigens expressed by organisms of the intestinal microbiome (1-4). For example, the anti-*Saccharomyces cerevisiae* antibody (ASCA) interacts with mannose epitopes of this yeast species and is present in 48% to 80% of patients with CD (5,6). In general, these markers are specific for IBD, but experience low sensitivity.

CD biomarkers can also be of value after the diagnosis is established, as measures of disease activity and predictors of outcome. The available serological markers have not proven useful in these contexts (7-13). Other serum and stool markers, such as C-reactive protein (CRP) and fecal calprotectin, are elevated in inflammatory and gastrointestinal diseases, but are not specific for IBD (14-19). The introduction of additional sensitive, specific, and noninvasive diagnostic markers may aid in the diagnosis of IBD, reduce patient risk and discomfort by reducing invasive testing, and accelerate the study of new treatments.

MicroRNAs (miRNAs) are short, noncoding RNAs that regulate target mRNAs via transcript degradation or translational repression. Cell- and tissue-specific miRNA expression profiles are altered in numerous disease states (20-30). The loss of all of the intestinal miRNA results in impaired barrier function and inflammation similar to IBD (31). With the exception of gastric and colorectal cancers (32,33), little is known regarding the function of miRNA in intestinal disease. Wu et al (34) profiled miRNA expression in colon biopsies in ulcerative colitis (UC), indeterminate colitis, infectious colitis, microscopic colitis, and irritable bowel syndrome. Significant changes were confirmed in 11 miRNAs in UC tissues when compared with normal controls, of which 5 were altered at least 2-fold. The authors focused on microRNA-192 (miR-192; 1.9-fold lower in active UC), showing that it localizes to colonic epithelia and is able to repress expression of the chemokine CXCL2 (MIP-2a) in a colonic epithelial cell line. They suggest that in UC, decreased miR-192 levels result in intestinal inflammation via increased CXCL2 secretion by epithelial cells. The same group has also investigated ileal and colonic miRNA expression, resulting in the identification of several miRNAs whose levels are altered in CD (35).

The recent discovery of circulating miRNAs possessing remarkable stability has prompted a number of studies investigating their potential merit as noninvasive biomarkers (36, 37). Specific circulating miRNA profiles have now been described for various conditions, particularly cancer (36-41). In some cases, these circulating miRNA profiles are known to correlate with miRNA expression changes in the diseased tissue (41,42). Additionally, changes in circulating miRNA profiles may precede those of standard blood biomarkers (39,41), and several disease-specific profiles are known to possess both diagnostic and prognostic value (43,44). Taken together, these properties implicate miRNAs to be attractive, blood-based, noninvasive biomarkers.

SUMMARY OF THE INVENTION

In accordance with the present invention, a method of determining increased risk of a human subject for developing inflammatory bowel disease (IBD) or increased likelihood of the presence of IBD in a human subject is provided. An exemplary method entails the steps of:
  (i) measuring in a sample from the subject the level of at least one, two, three, four, five, six, seven, eight, or more or all of the differentially expressed miRNA provided in FIG. 1; and
  (ii) comparing the level of the miRNA in the sample of step i) to a level present in a control sample and/or at least one internal reference miRNAs (e.g., miR-150 and/or miR-342-3p), wherein an increase in the level of the miRNA in the sample relative to the control levels of step ii) is indicative of the subject either having increased risk of developing IBD or increased likelihood of the presence of IBD. In certain embodiments, the increased level of expression of said miRNA(s) is correlated with the presence of Crohn's disease. In a particular embodiment, the differentially expressed miRNA are the miRNAs with the greatest difference in expression in FIG. 1.

Also provided is a method of determining a patient's response to IBD therapy. An exemplary method entails the steps of:
  (i) measuring in a serum sample from the subject the level of at least one, two, three, four, five, six, seven, eight, or more or all of the differentially expressed miRNA provided in FIG. 1, and administering a therapeutic agent useful for the treatment of IBD to said subject, and
  (ii) comparing the level of the miRNA in the sample of step i) to levels present before and/or after treatment, wherein a decrease in the level of at least one miRNA gene product in the sample relative to pretreatment levels of step ii) is indicative that said therapeutic agent is useful for the treatment of IBD. In a particular embodiment, the differentially expressed miRNA are at least one, two, three, four, five, 10 or all of the miRNA with the greatest difference in expression in FIG. 1.

Finally, a panel of differentially expressed miRNAs having utility in diagnostic and therapeutic assays for IBD, particularly Crohn's disease are provided. Such miRNAs or nucleic acids hybridizing to the same can be in solution, may optionally be detectably labeled, and/or may be affixed to a solid support.

DETAILED DESCRIPTION OF THE INVENTION

Figure 1A:
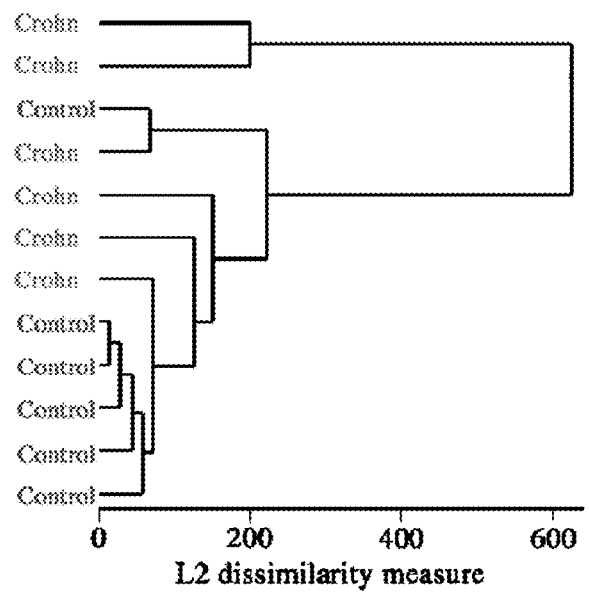
FIG. 1A-1C. Low-density array (LDA) analysis of serum miRNA in patients with pediatric CD. A, Dendrogram showing hierarchical cluster analysis using 68 miRNAs detected in all samples by LDA. B, Scatterplot of relative serum miRNA levels of 11 CD-associated miRNAs and 2 unaltered control miRNAs as determined by LDA and individual qRT-PCR. Open circles, control samples; filled circles, CD samples; r, Spearman rank correlation coefficient. C, Comparison of relative levels of CD-associated miRNAs in control and CD samples determined by individual qRT-PCR. Data are presented as fold change in comparison with controls. *P<0.05. CD=Crohn disease; LDA=low-density array; miRNA=microRNA; qRT-PCR=quantitative reverse transcription-polymerase chain reaction.

Circulating miRNAs have been identified which serve sensitive and specific indicators of Crohn's disease in children. These miRNAs are present in cell-free preparations of serum or plasma. Advantages of using serum miRNA as a biomarker(s) include its stability for several hours at room temperature and through multiple freeze/thaw cycles and its low variation among normal individuals. Thus, in accordance with the present invention, a novel non-invasive assay for biomarkers for IBD is disclosed. This assay provides for 1) prompt and accurate diagnosis, essential for the initiation of medical therapy, 2) is effective to distinguish CD from UC and other conditions in connection with a diagnosis of IBD and is 3) able to facilitate prediction of outcomes which are needed to guide the selection of therapy from the range of options available. Finally, characterization of the miRNA panel disclosed herein enables the development of novel therapies which can be targeted to such markers. While a number of IBD biomarkers have been described, they are limited by poor sensitivity, poor correlation with disease activity, and/or cost.

DEFINITIONS

The phrase "inflammatory bowel disease or IBD" refers to primarily ulcerative colitis (UC) and Crohn's (CD). These are chronic conditions of uncertain etiology, characterized by recurrent episodes of abdominal pain, often with diarrhea. Although both ulcerative colitis and Crohn's disease have distinct pathologic findings, a significant percentage of patients with inflammatory bowel disease (IBD) have indeterminate findings. Crohn's disease is also referred to a regional enteritis, terminal ileitis, or granulomatous ileocolitis.

"MicroRNAs or miRNAs" refers to a family of small approximately twenty two nucleotide noncoding RNAs. They are transcribed from specific genes and generally undergo two cleavage steps that result in mature miRNAs. MiRNAs cause post-transcriptional gene repression by increasing mRNA degradation or by inhibiting translation.

As used herein, the term "miR-specific inhibitor" refers to a nucleic acid molecule that is complementary, or essentially complementary to at least a portion of a microRNA molecule and inhibits its binding or activity towards its target gene transcripts. A miR-specific inhibitor may interact with the miRNA directly or may interact with the miRNA binding site in a target transcript, preventing its interaction with a miRNA. In some embodiments, the miR-specific inhibitor comprises a nucleotide sequence of at least 5 consecutive nucleotides, at least 6 consecutive nucleotides, at least 7 consecutive nucleotides, at least 8 consecutive nucleotides, or at least 9 nucleotides that are complementary to the seed region of a microRNA molecule (i.e. within positions 1 to 10 of the 5' end of the microRNA molecule). In a particular embodiment, the miR-specific inhibitor may comprise a nucleotide sequence of at least 6 consecutive nucleotides that are complementary to the seed region of a microRNA molecule at positions 2-8. These consecutive nucleotides complementary to the microRNA seed region may also be referred to as microRNA binding sites.

A miR-specific inhibitor may be a single stranded molecule. The miR-specific inhibitor may be chemically synthesized or may be encoded by a plasmid. In some embodiments, the miR-specific inhibitor comprises RNA. In other embodiments, the miR-specific inhibitor comprises DNA. In other embodiments, the miR-specific inhibitor may encompass chemically modified nucleotides and non-nucleotides. See, e.g. Brennecke et al., 2005, PLOS Biol. 3(3): pe85.

In some embodiments, a miR-specific inhibitor may be an anti-miRNA (anti-miR) oligonucleotide (see WO2005054494; Hutvagner et al., 2004, PLoS Biol. 2:E98; Orom et al., 2006, Gene 372:137-141). Anti-miRs may be single stranded molecules. Anti-miRs may comprise RNA or DNA or have non-nucleotide components. Alternative embodiments of anti-miRs may be as described above for miR-specific inhibitors. Anti-miRs anneal with and block mature microRNAs through extensive sequence complementarity. In some embodiments, an anti-miR may comprise a nucleotide sequence that is a perfect complement of the entire miRNA. In some embodiments, an anti-miR comprises a nucleotide sequence of at least 6 consecutive nucleotides that are complementary to a microRNA molecule at positions 2-8 and has at least 50%, 60%, 70%, 80%, or 90% complementarity to the rest of the miRNA. In other embodiments, the anti-miR may comprise additional flanking sequence, complimentary to adjacent primary (pri-miRNA) sequences. Chemically modified anti-miRs are commercially available from a variety of sources, including but not limited to Sigma-Proligo, Ambion, Exiqon, and Dharmacon.

"miRNA mimics" are chemically synthesized nucleic acid based molecules, preferably double-stranded RNAs which mimic mature endogenous miRNAs after transfection into cells.

The term "genetic alteration" refers to a change from the wild-type or reference sequence of one or more nucleic acid molecules. Genetic alterations include without limitation, base pair substitutions, additions and deletions of at least one nucleotide from a nucleic acid molecule of known sequence.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the functional and novel characteristics of the sequence.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to a miRNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligoribonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., Molecular Cloning, Cold Spring Harbor Laboratory (1989):

$$T_m = 81.5° C. + 16.6 \text{ Log } [Na+] + 0.41(\% \, G+C) - 0.63(\% \text{ formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 μg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 μg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 μg/ml denatured salmon sperm DNA at 42° C., and washed in 0.1× SSC and 0.5% SDS at 65° C. for 15 minutes. The term "oligonucleotide," as used herein is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length. Typical miRNAs are approximately 22 ribonucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the nucleic acid molecule of interest such that the latter is transcribed into mRNA. Host cell machinery then translates mRNA into a polypeptide.

Those skilled in the art will recognize that a nucleic acid vector can contain nucleic acid elements other than the promoter element and the nucleic acid molecule of interest. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, polyA addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism," or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein.

This term refers primarily to a protein produced by expression of an isolated nucleic acid molecule. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably between 20 and 30 nucleotides and most preferably 22 nucleotides long.

"Sample" or "patient sample" or "biological sample" generally refers to a sample which may be tested for a particular molecule. Samples may include but are not limited to cells, body fluids, including, blood, serum, plasma, urine, saliva, gastrointestinal fluid and the like.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include miRNA, shRNA, antisense oligonucleotides, peptides, peptide/DNA complexes, and any nucleic acid based molecule which exhibits the capacity to modulate the activity of the target nucleic acids described herein or their encoded proteins. Agents are evaluated for potential biological activity by inclusion in screening assays described hereinbelow.

Methods for Diagnosing a Propensity for the Development of IBD

The discovery that certain microRNA molecules are differentially expressed in patients having IBD provides the means to diagnose or detect a propensity for developing such a disorder. Levels of expression of the other differentially expressed miRNAs provided in FIG. 1 can be assessed in biological samples of interest. In one embodiment expression levels of at least one, two, three, four, five, six, seven, eight, nine, ten, or more miRNAs are determined. In a particular embodiment, expression of the miRNA with the greatest difference in expression is determined. In a particular embodiment, expression levels of miRNAs isolated from the patient are then compared to levels previously determined to be indicative of the presence of CD. In a particular embodiment, the IBD-associated miRNA levels are compared to the patient's own levels of miR-150 and/or miR-342-3p (the internal reference miRNAs), thereby eliminating the need for comparison to a control sample. Assays for detecting miRNA expression levels may be conducted on any type of biological sample, including but not limited to body fluids (including serum, gastrointestinal fluid, and sputum), any type of cell (such as intestinal cells, white blood cells, mononuclear cells) or body tissue. In preferred embodiments miRNA levels are assessed in serum samples.

In certain embodiments for screening for IBD associated miRNAs, the miRNA will be identified using new detection technologies which enable analysis of small samples containing 1 µg of total RNA or less. For example, ABI Taqman provides a kit and method employing 10 ng of total RNA for miRNA reverse transcription. Using Resonance Light Scattering (RLS) technology, as opposed to traditional fluorescence techniques, multiple reads can detect low quantities of RNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Thus any of the aforementioned techniques may be used to detect or quantify IBD associated miRNA marker expression and accordingly, diagnose a propensity for developing an inflammatory disorder such as IBD.

Kits and Articles of Manufacture

Any of the aforementioned products can be incorporated into a kit which may contain a positive control miRNA or one or more such markers immobilized on a Gene Chip, one or more oligonucleotides, optionally detectably labeled and hybridizing to at least one miRNA disclosed herein, a polypeptide, a peptide, an antibody, a label, marker, or reporter, a pharmaceutically acceptable carrier, a physiologically acceptable carrier, instructions for use, a container for serum, a vessel for administration, an assay substrate, or any combination thereof.

Methods of Using miRNA Modulation for Development of Therapeutic Agents

The present inventors have discovered that several miRNA molecules are differentially expressed in IBD patients which are detectable in serum samples. Notably, these miRNA molecules exhibit homology to a variety of proteins involved in the modulation and control of inflammation and thus can be used to advantage as therapeutics to inhibit or reduce the aberrant inflammatory pathways observed in a variety of different medical disorders. Such agents will have utility for the treatment of a variety of disorders including inflammatory disorders, such as IBD.

Molecular modeling should facilitate the identification of specific organic molecules which mimic the action of the mRNAs disclosed herein and the other differentially expressed miRNA disclosed herein. A combinatorial chemistry approach will be used to identify molecules with greatest activity and then iterations of these molecules will be developed for further cycles of screening. In certain embodiments, candidate drugs can be screened from large libraries of synthetic or natural compounds. One example is an FDA approved library of compounds that can be used by humans. In addition, compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd. (Moscow, Russia), Princeton Biomolecular (Monmouth Junction, N.J.), Scientific Exchange (Center Ossipee, N.H.), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China).

Libraries of natural compounds in the form of bacterial, fungal, plant and animal extracts are commercially available or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Several commercial libraries can be used in the screens.

The agents employed in drug screening assays may either be free in solution, affixed to a solid support or within a cell. One method of drug screening utilizes eukaryotic or prokaryotic host cells which are stably transformed with recombinant polynucleotides expressing the miRNA or a mimic thereof preferably in competitive binding assays. Such cells, either in viable or fixed form, can be used for standard binding assays. One may determine, for example, formation of complexes between the miRNA and the agent being tested, or examine the degree to which the formation of a complex between the miRNA and the 3' end of the target mRNA is interfered with by the agent being tested.

A further technique for drug screening involves the use of host eukaryotic cell lines or cells (such as described above) which have a nonfunctional or altered IBD associated miRNA molecule(s). These host cell lines or cells exhibit defective miRNA function. The host cell lines or cells are grown in the presence of drug compound, the cells are then assessed for any alteration induced by the compound in the treated cells relative to the untreated cells. Host cells contemplated for use in the present invention include but are not limited to mammalian cells, particularly cell types present in gastrointestinal tract. Methods for introducing nucleic acid molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

A wide variety of expression vectors are available that can be modified to express the miRNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in *Saccharomyces* are also described in Current Protocols in Molecular Biology (1989).

Promoters for use in expression vectors of this invention include promoters that are operable in eukaryotic cells. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, *Picchia* promoters such as the alcohol oxidase promoter, and *Saccharomyces* promoters such as the gal4 inducible promoter and the PGK constitutive promoter, and the Thy-1 promoter. In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the miRNAs of the present invention provide a system in which to screen potential compounds or agents for the ability to modulate the development of inflammation. Thus, in one embodiment, the nucleic acid molecules of the invention may be used to create recombinant cell lines for use in assays to identify agents which modulate aspects of the inflammatory bowel disease pathway.

In another embodiment, the identification of the differentially expressed miRNAs involvement in inflammatory processes in the bowel enables the production of strains of laboratory mice which express altered levels of such miRNAs. Transgenic mice expressing these miRNA molecules provide a model system in which to examine the role of the miRNA in the development and progression towards IBD. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role that a target protein plays in various cellular inflammatory processes. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extra-chromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of miRNA encoding nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated miRNA encoding genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its nonhomologous insertion with effective herpes drugs such as gancyclovir (GANC) or (1-(2-deoxy-2-fluoro-B-D arabinofluranosyl)-5-iodouracil, (FIAU). By this counter selection, the number of homologous recombinants in the surviving transformants can be increased.

As used herein, a knock-in animal is one in which the endogenous murine gene, for example, has been replaced with human miRNA encoding gene of the invention. Such knock-in animals provide an ideal model system for studying the development of IBD.

As used herein, the expression of a miRNA encoding nucleic acid can be targeted in a "tissue specific manner" or "cell type specific manner" using a vector in which nucleic acid sequences encoding the miRNA are operably linked to regulatory sequences (e.g., promoters and/or enhancers) that direct expression of the encoded miRNA in a particular tissue or cell type. Such regulatory elements may be used to advantage for both in vitro and in vivo applications. Promoters for directing tissue specific proteins are well known in the art and described herein.

The nucleic acid sequence encoding the miRNA may be operably linked to a variety of different promoter sequences for expression in transgenic animals. Such promoters include, but are not limited to a Thy-1 promoter; a PGK promoter; and a CMV promoter. Methods of use for the transgenic mice of the invention are also provided herein. Transgenic mice into which a nucleic acid encoding the miRNA has been introduced are useful, for example, to develop screening methods to identify therapeutic agents capable of modulating the development of IBD.

In other approaches, miRNAs can be administered to such mice and the effects on inflammatory disease modulation assessed. Alternatively, agents which inhibit expression of such miRNAs can also be tested in this in vivo model and the effects on colon disease determined.

Pharmaceuticals and miRNA Therapies

The elucidation of the role played by miRNAs on inflammation as described herein facilitates the development of pharmaceutical compositions useful for treatment and diagnosis of inflammatory disorders such as IBD. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

Certain miRNAs described herein may be used for treatment. They may optionally be linked to a membrane permeant sequence. A "membrane permeant peptide sequence" refers to a peptide sequence which is able to facilitate penetration and entry of the miRNA across the cell membrane. Exemplary peptides include without limitation, the signal sequence from Kaposi fibroblast growth factor, the HIV tat peptide (Vives et al., J Biol. Chem., 272:16010-16017, 1997), Non-toxic membrane translocation peptide from protamine (Park et al., FASEB J. 19(11):1555-7, 2005), CHARIOT® delivery reagent (Active Motif; U.S. Pat. No. 6,841,535) and the antimicrobial peptide Buforin 2.

In one embodiment of the invention miRNAs are delivered for therapeutic benefit. There are several ways to administer the miRNA of the invention in vivo to treat inflammatory disorders such as IBD, including, but not limited to, naked miRNA delivery, miRNA conjugation and delivery, liposome carrier-mediated delivery, polymer carrier delivery, nanoparticle compositions, plasmid-based methods, and the use of viruses.

miRNA compositions of the invention can comprise a delivery vehicle, including liposomes, for administration to a subject, carriers and diluents and their salts, and/or may be present in pharmaceutically acceptable formulations. This can be necessary to allow the miRNA to cross the cell membrane and escape degradation. Methods for the delivery of nucleic acid molecules are described in Akhtar et al., 1992, Trends Cell Bio., 2, 139; Delivery Strategies for Antisense Oligonucleotide Therapeutics, ed. Akhtar, 1995, Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192; Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule.

The frequency of administration of the miRNA to a patient will also vary depending on several factors including, but not limited to, the type and severity of the inflammatory disorder to be treated, the route of administration, the age and overall health of the individual, the nature of the miRNA, and the like. It is contemplated that the frequency of administration of the miRNA to the patient may vary from about once a month, to about once a week, to about once per day, to about several times daily.

Pharmaceutical compositions that are useful in the methods of the invention may be administered systemically in parenteral, oral solid and liquid formulations, ophthalmic, suppository, aerosol, topical or other similar formulations. In addition to the appropriate miRNA, these pharmaceutical compositions may contain pharmaceutically-acceptable carriers and other ingredients known to enhance and facilitate drug administration. Thus such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to administer the appropriate miRNA to a patient according to the methods of the invention. The use of nanoparticles to deliver miRNAs, as well as cell membrane permeable peptide carriers that can be used are described in Crombez et al., Biochemical Society Transactions v35:p44 (2007).

One skilled in the art appreciates that a pharmaceutical composition comprising the differentially expressed miRNAs or mimics thereof can be administered to a subject by various routes including, for example, orally or parenterally, such as intravenously (i.v.), intramuscularly, subcutaneously, intraorbitally, intranasally, intracapsularly, intraperitoneally (i.p.), intracisternally, intra-tracheally (i.t.), or intra-articularly or by passive or facilitated absorption. The same routes of administration can be used other pharmaceutically useful compounds, for example, small molecules, nucleic acid molecules, peptides, antibodies and polypeptides as discussed hereinabove.

A pharmaceutical composition comprising such differentially expressed miRNAs or or mimic also can be incorporated, if desired, into liposomes, microspheres, microbubbles, or other polymer matrices (Gregoriadis, Liposome Technology, Vols. I to III, 2nd ed., CRC Press, Boca Raton Fla. (1993)). Liposomes, for example, which consist of phospholipids or other lipids, are nontoxic, physiologically acceptable and metabolizable carriers that are relatively simple to make and administer.

Expression vectors for the expression of miRNA or mimic molecules preferably employ a strong promoter which may be constitutive or regulated. Such promoters are well known in the art and include, but are not limited to, RNA polymerase II promoters, the T7 RNA polymerase promoter, and the RNA polymerase III promoters U6 and H1 (see, e.g., Myslinski et al. (2001) Nucl. Acids Res., 29:2502 09).

Nucleic acid molecules can be administered to cells by incorporation into other vehicles, such as biodegradable polymers, hydrogels, cyclodextrins. (see for example Gonzalez et al., 1999, Bioconjugate Chem., 10, 1068-1074; Wang et al., International PCT publication Nos. WO 03/47518 and WO 03/46185), poly(lactic-co-glycolic) acid (PLGA) and PLCA microspheres (see for example U.S. Pat. No. 6,447,796 and US Patent Application Publication No. US 2002130430), biodegradable nanocapsules, and bioadhesive microspheres, or by proteinaceous vectors (O'Hare and Normand, International PCT Publication No. WO 00/53722)

Cationic lipids and polymers are two classes of non-viral miRNA or mimic delivery which can form complexes with negatively charged miRNA or mimic. The self-assembly PEGylated polycation polyethylenimine (PEI) has also been used to condense and protect miRNAs (Schiffelers et al., 2004, Nuc. Acids Res. 32: 141-110). The miRNA or mimic complex can be condensed into a nanoparticle to allow efficient uptake of the miRNA or mimic through endocytosis. Also, the nucleic acid-condensing property of protamine has been combined with specific antibodies to deliver miRNAs or mimics and can be used in the invention (Song et al., 2005, Nat Biotech. 23:709-717).

A pharmaceutical composition comprising miRNA can be administered as an aerosol formulation which contains the miRNA in dissolved, suspended or emulsified form in a propellant or a mixture of solvent and propellant. The aerosolized formulation is then administered through the respiratory system or nasal passages.

In an individual suffering from an inflammatory disease, in particular a more severe form of the disease, administration of a miRNA can be particularly useful when administered in combination, for example, with a conventional agent for treating such a disease or with another miRNA which modulates expression or function of a protein which plays a role in the inflammatory process. The skilled artisan would administer a miRNA, alone or in combination with a second agent or miRNA, based on the clinical signs and symptoms exhibited by the individual and would monitor the effectiveness of such treatment using routine methods.

A miRNA can be administered in combination with steroidal anti-inflammatory agents including corticosteroids, for example, dexamethasone, beclomethasone, fluticasone, triamcinolone and budesonide. A miRNA can also be administered in combination with non-steroidal anti-inflammatory agents such as aspirin (acetylsalicylic acid), indomethacin, ibuprofen, naproxen, diclofenac, sulindac, oxaprozin, diflunisal, bromfenac, piroxicam, etodolac and fenoprofen. A miRNA can also be administered with other immune modifiers such as inhibitors or agonists of cytokine receptors, antibodies directed against cytokines or their receptors or agents that act on immune system signal transduction pathways. When a miRNA is used with another anti-inflammatory agent, either or both of the miRNA and anti-inflammatory agent can generally be administered at a lower dosage.

When a miRNA is administered in combination with one or more other anti-inflammatory agent, the miRNA and other anti-inflammatory agent can be co-administered in the same formulation. Alternatively, the miRNA and other anti-inflammatory agent can be administered simultaneously in separate formulations. Administration of the pharmaceutical preparation is preferably in a "prophylactically effective amount" or a "therapeutically effective amount" (as the case may be, although prophylaxis may be considered therapy), this being sufficient to show benefit to the individual. This amount prevents, alleviates, abates, or otherwise reduces the severity of IBD symptoms in a patient.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

The following materials and methods are provided to facilitate the practice of the present invention.

Serum Samples

Sera from patients with pediatric CD and healthy controls were obtained as part of institutional review board-approved studies at the Children's Hospital of Philadelphia Research Institute (M.T. and M.B.L.); CD diagnosis was confirmed by standard parameters as previously described (47-49). Site of disease was defined according to the Montreal classification (50). CD activity was assessed using the Pediatric Crohn Disease Activity Index (PCDAI) (51). Controls were recruited for studies of growth and nutrition, had normal height and body mass index, and had no history of chronic diseases. Characteristics of patients with CD and controls are summarized in Table 1. Pediatric celiac disease serum samples and controls were obtained from Dr Alessio Fasano of the University of Maryland School of Medicine. Samples with visible evidence of hemolysis were excluded from the study. Serum was stored at −80° C. until RNA isolation.

TABLE 1

Baseline characteristics in patients with CD and controls

| | CD (n = 46) | Controls (n = 32) |
|---|---|---|
| Age, y | 13.7 ± 3.0 | 13.1 ± 4.1 |
| Sex, male, % | 65.2 | 53.1 |
| Race, white, % | 84.8* | 65.6 |
| PCDAI | 34.7 ± 18.1 | |
| Median (range) | 32.5 (7.5, 80) | |
| No active disease (≤slO), % | 6.5 | |
| Mild disease (11-30), % | 39.1 | |
| Moderate/severe (>30), % | 54.3 | |
| Months since diagnosis | 1.0 ± 1.9 | |
| Site of disease, n (%) | | |
| Isolated ileal disease | 0 | |
| Isolated colonic disease | 1 (2) | |
| Heccolonic disease | 28 (61) | |
| Isolated upper GI tract disease | 1 (2) | |
| Perirectal involvement | 21 (46) | |
| Colonic involvement | 45 (98) | |
| Heal involvement | 29 (63) | |
| Duodenal involvement | 13 (28) | |
| Gastric involvement | 40 (87) | |
| Esophageal involvement | 22 (48) | |

Continuous variables presented as mean ± standard deviation unless otherwise indicated.
Subjects may be counted in multiple disease site subgroups.
CD = Crohn disease;
GI = gastrointestinal;
PCDAI = pediatric Crohn disease activity index.
*P < 0.05 compared with controls.

RNA Isolation

Total RNA was isolated from 60 mL of serum using the mirVana miRNA Isolation Kit (Ambion, Austin, Tex.) according to manufacturer's instructions. Exogenous *Caenorhabditis elegans* and human miRNAs were added as normalizing controls immediately following serum denaturation. RNA was eluted with 100 mL elution solution (95° C.) and stored at −80° C. Quality of total RNA preparations was confirmed using the Agilent 2100 Bioanalyzer with the RNA 6000 Pico kit (Agilent Technologies, Santa Clara, Calif.).

miRNA Analysis by Low-density Array

TaqMan Human MicroRNA Arrays (Applied Biosystems, Foster City, Calif.) were used to quantify serum miRNA content according to the manufacturer's instructions. Reverse transcription (RT) products were preamplified and arrays were processed and analyzed by the ABI PRISM 7900HT Sequence Detection System (Applied Biosystems). miRNA levels were normalized against exogenous human embryonic-specific miRNAs (miR-302a and miR-372 for pool A arrays and miR-302d for pool B arrays) added in equal amounts during RNA isolation to control for assay variability (52).

qRT-PCR

RNA volumes of 1.334 were reverse transcribed and amplified using the TaqMan MicroRNA Reverse Transcription and miRNA Assay Kits (Applied Biosystems) according to the manufacturer's instructions. Reactions were performed in duplicate. miRNA levels were normalized to the levels of 2 exogenous *C. elegans* miRNAs lacking homology to human sequences (celmiR-54 and cel-miR-238) added during RNA isolation (36).

Enzyme-Linked Immunosorbent Assay

Serum levels of CRP and ASCA IgG were determined in control and patients with CD using commercial enzyme-linked immunosorbent assay Kits (Calbiotech, Spring Valley, Calif.; ALPCO, Salem, N.H.) according to the manufacturer's instructions.

Statistical Analysis

Significantly altered miRNAs from the low-density array (LDA) experiment were identified using Significance Analysis of Microarrays software (Stanford University, Stanford, Calif.). All other statistical calculations were performed using Stata 11.0 (StataCorp, College Station, Tex.). Fisher exact test, Mann-Whitney test, and Wilcoxon matched-pairs signed rank test were used to determine significance. Hierarchical cluster analysis (complete-linkage clustering with Euclidean (L2) distance) was performed using the 68 miRNAs detected in all 12 LDA samples. Receiver operating characteristic (ROC) curve analyses were used to determine diagnostic utility. Correlation between miRNAs was determined by Spearman correlation The following examples are provided to facilitate the practice of the present invention. They are not intended to limit the invention in any way.

EXAMPLE I

Discovery of CD-associated Circulating miRNA Using Low-Density Array qRT-PCR

A microfluidic quantitative reverse transcription-polymerase chain reaction (qRT-PCR)

Figure 1B:
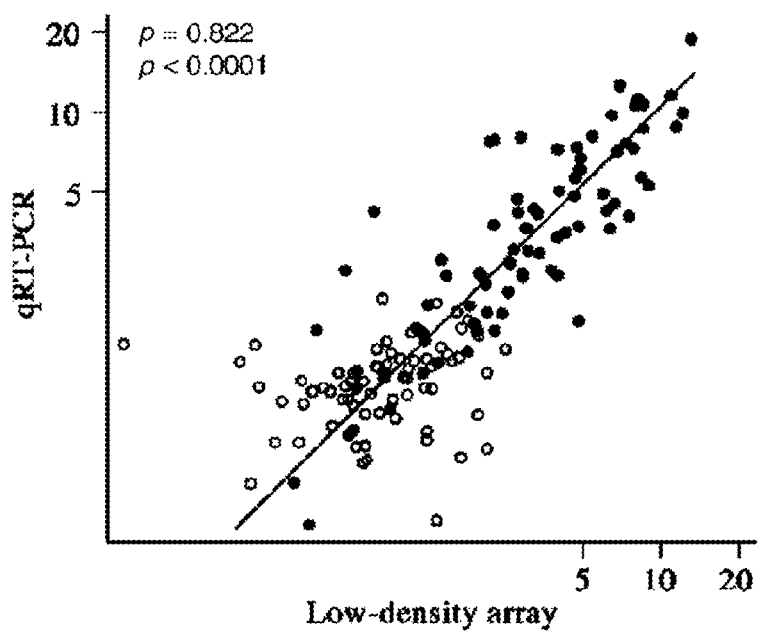
Figure 1C:
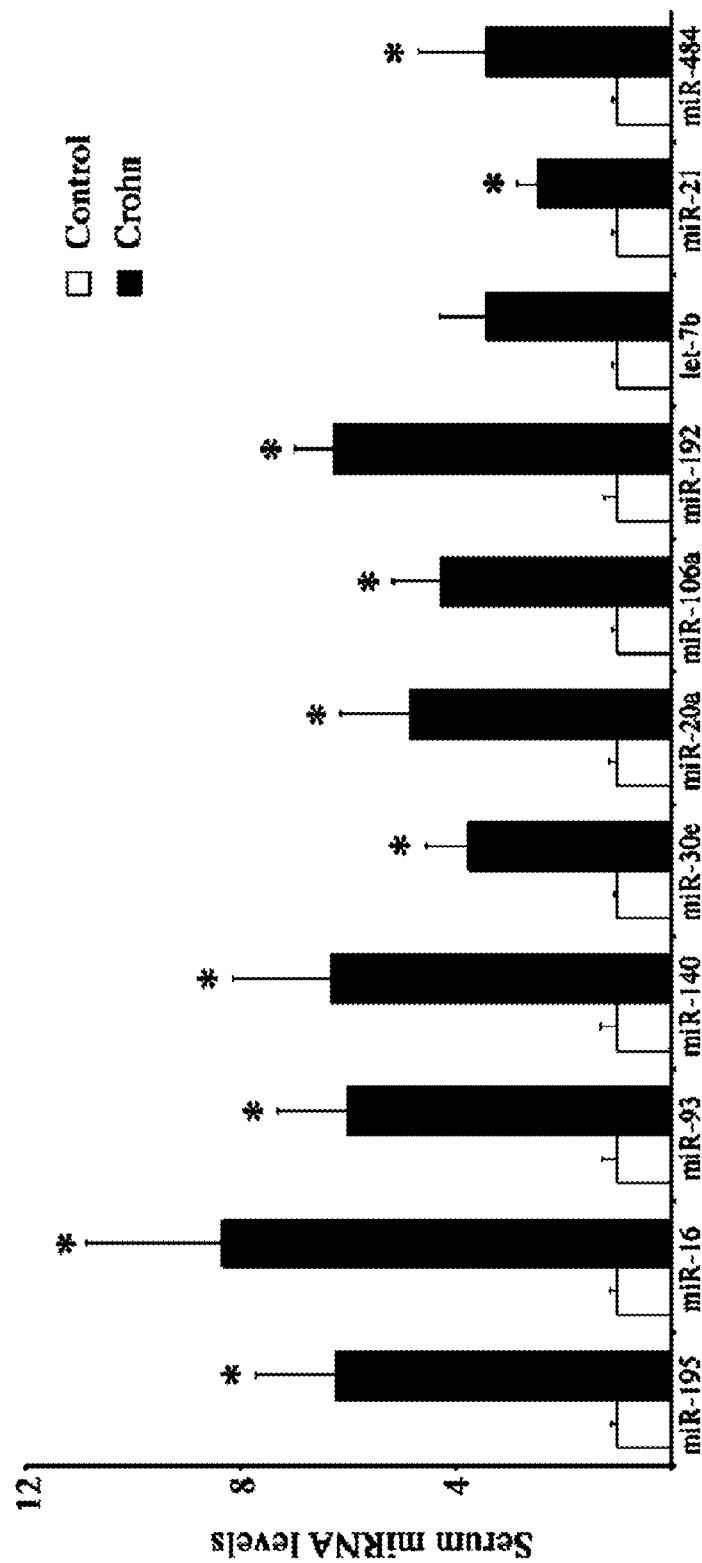

LDA platform capable of detecting 667 mature human miRNAs was used to identify CD-associated miRNAs in an exploratory cohort of patients with CD with active disease (12.5±1.4 years, 67% boys, PCDAI=32.5±8.4, n=6), compared with age- and sex-matched healthy controls. Hierarchical clustering analysis revealed altered serum miRNA profiles in patients with CD compared with controls (FIG. 1A). Differences in individual serum miRNA levels between groups were identified using significance analysis of microarrays (54). A total of 24 miRNAs were increased at least 50% in patients with CD at a false discovery rate of 6%. Ten of the 24 miRNAs are members of 3 paralogous genomic miRNA clusters with oncogenic properties, namely miR-17-92, miR-106b-25, and miR-106a-363 (55-57). No circulating miRNAs were significantly decreased in patients with CD. A panel of 11 miRNAs was selected for direct confirmation by qRT-PCR; a single member (miR-20a, miR-93, and miR-106a) from each of the 3 paralogous miRNA clusters was included. Good agreement was observed between the array and individual qRT-PCR validation results (FIG. 1B). All but 1 of the selected miRNAs was significantly increased in the CD sera at least 2.5-fold (FIG. 1C).

Confirmation of CD-Associated Circulating miRNA in an Independent Sample Set

Figure 2A:
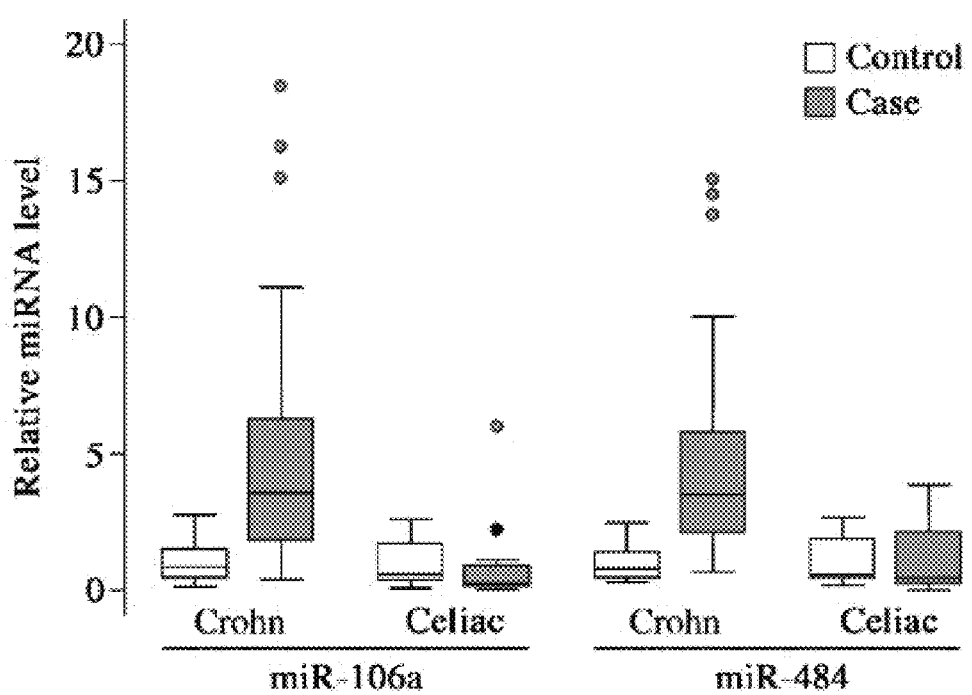
FIG. 2A-2B. Validation of CD-associated circulating miRNAs. A, Box-whisker plots of CD-associated serum miRNAs validated in an independent set of controls (n=32) and CD cases (n=46) as well as celiac cases (n=12) and associated controls (n=12). Box, 25% to 75%; whisker, upper, lower adjacent values; line, median; points, outside values. Data are presented as fold change in comparison with controls. B, Receiver operating characteristic curves of 2 CD-associated miRNAs in sera of patients with pediatricCD (n=46) and healthy controls (n=32). AUC=area under the curve; CD=Crohn disease; miRNAs=microRNAs.

To verify the differences in serum miRNA levels between patients with CD and controls, qRT-PCR was performed on a larger, distinct set of incident cases of CD (n=46), similar to the exploratory cohort in terms of demographic and disease characteristics, and control subjects (n=46) (Table 1). Each of the selected 11 miRNAs was significantly elevated (range 2.7- to 8.7-fold) in the serum of patients with CD compared with controls at a P<0.0001 (Table 2). The results from miR-106a and miR-484 are illustrated in FIG. 2A. No correlation was observed between miRNA levels or white or red blood cell count, indicating that the altered miRNA levels are not a simple reflection of hematologic changes. The miRNA levels also did not correlate with the albumin concentration, erythrocyte sedimentation rate, or CRP level (data not shown).

Because CD sera were compared with sera of healthy control patients, it is possible that the observed elevations in panel miRNAs occur during enteritis of any kind To address this possibility, miRNA levels were measured in the sera of children with active celiac disease and age-, race-, and sex-matched controls without celiac disease (Table 3). All 11 panel miRNAs elevated in CD serum were unaltered in the serum of celiac patients in comparison with healthy controls (Table 2 and FIG. 2A). The data suggest that elevated levels of the CD-associated circulating miRNAs are not a general result following intestinal tract inflammation and destruction, because active celiac disease involves inflammatory-mediated damage to the proximal small bowel mucosa.

TABLE 2

Serum miRNAs in patients with Crohn and celiac disease compared with controls

| | Fold change | |
|---|---|---|
| miRNA | Crohn (n = 46) | Celiac (n = 12) |
| miR-16 | 8.74 ± 1.54* | 1.04 ± 0.60 |
| let-7b | 7.49 ± 1.32* | 1.19 ± 0.73 |
| miR-195 | 5.67 ± 0.90* | 0.95 ± 0.53 |
| miR-106a | 4.79 ± 0.63* | 0.98 ± 0.49 |
| miR-20a | 4.63 ± 0.63* | 0.90 ± 0.42 |
| miR-30e | 4.60 ± 0.59* | 0.96 ± 0.34 |
| miR-140 | 4.51 ± 0.65* | 0.96 ± 0.37 |
| miR-484 | 4.50 ± 0.51* | 1.23 ± 0.44 |
| miR-93 | 4.48 ± 0.60* | 0.87 ± 0.49 |
| miR-192 | 4.24 ± 0.74* | 0.87 ± 0.27 |
| miR-21 | 2.72 ± 0.24* | 0.73 ± 0.27 |

Fold change is relative to controls and presented as mean ± SE.
*P < 0.0001.

TABLE 3

Baseline characteristics in patients with celiac disease and controls

| | Controls (n = 12) | Celiac disease (n = 12) |
|---|---|---|
| Age, y | 14.0 ± 0.7 | 14.0 ± 0.8 |
| Sex, male, % | 25.0 | 25.0 |
| Race, white, % | 100 | 100 |
| EMA positive, % | 0 | 100* |
| tTG-IgA, U/mL | 0.8 ± 0.1 | 38.8 ± 8.5* |

TABLE 3-continued

Baseline characteristics in patients with celiac disease and controls

| | Controls (n = 12) | Celiac disease (n = 12) |
|---|---|---|
| AGA-IgG, U/mL | 9.9 ± 2.0 | 19.5 ± 6.0 |
| AGA-IgA, U/mL | 3.9 ± 1.0 | 8.1 ± 2.4 |

Continuous variables presented as mean ± SE,
AGA = anti-gliadin anti-body;
EMA = anti-endomysial antibody;
tTG = anti-tissue transglutaminase antibody.
*P < 0.05 compared with controls.

Spearman rank correlation revealed that each CD-associated miRNA was positively correlated (P<0.0001) with each of the other CD-associated miRNAs. Among the miRNAs, the strongest miRNA-miRNA correlation (r=0.983) was between miR-20a and miR-106a, members of the paralogous clusters miR-17-92 and miR-106a-363, respectively, whereas the lowest correlation (r=0.709) was between miR-192 and miR-484 In contrast, levels of CD-associated miRNAs did not correlate with disease activity as determined by PCDAI score. Interestingly, esophageal disease involvement was significantly associated with higher serum levels of 8 CD-associated miRNAs (all except miR-16, miR-192, and let-7b; P<0.05).

Clinical Performance of Circulating miRNA as a Biomarker for CD

Figure 2B:
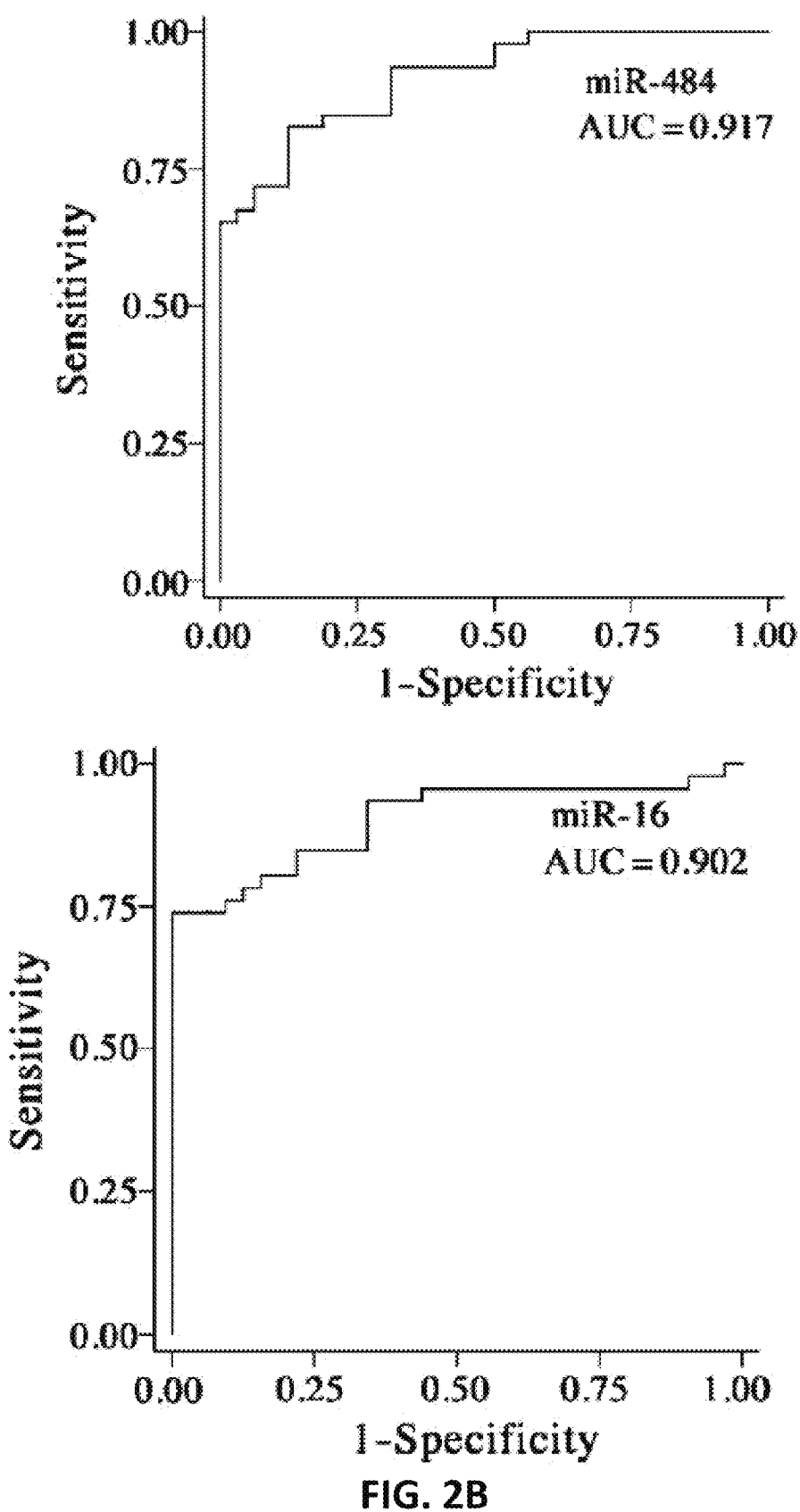

To assess the diagnostic utility of CD-associated miRNAs, we determined their receiver operating characteristics. ROC curves revealed that the CD-associated miRNAs have promising diagnostic properties, with area under the ROC curve (AUC) values of 0.82 to 0.92 (Table 4 and FIG. 2B), sensitivities of 70% to 83%, and specificities of 75% to 100% (Table 5). These values compared favorably to those of erythrocyte sedimentation rate and serum levels of CRP, ASCA IgG, and albumin, using standard diagnostic thresholds.

Figure 3A:
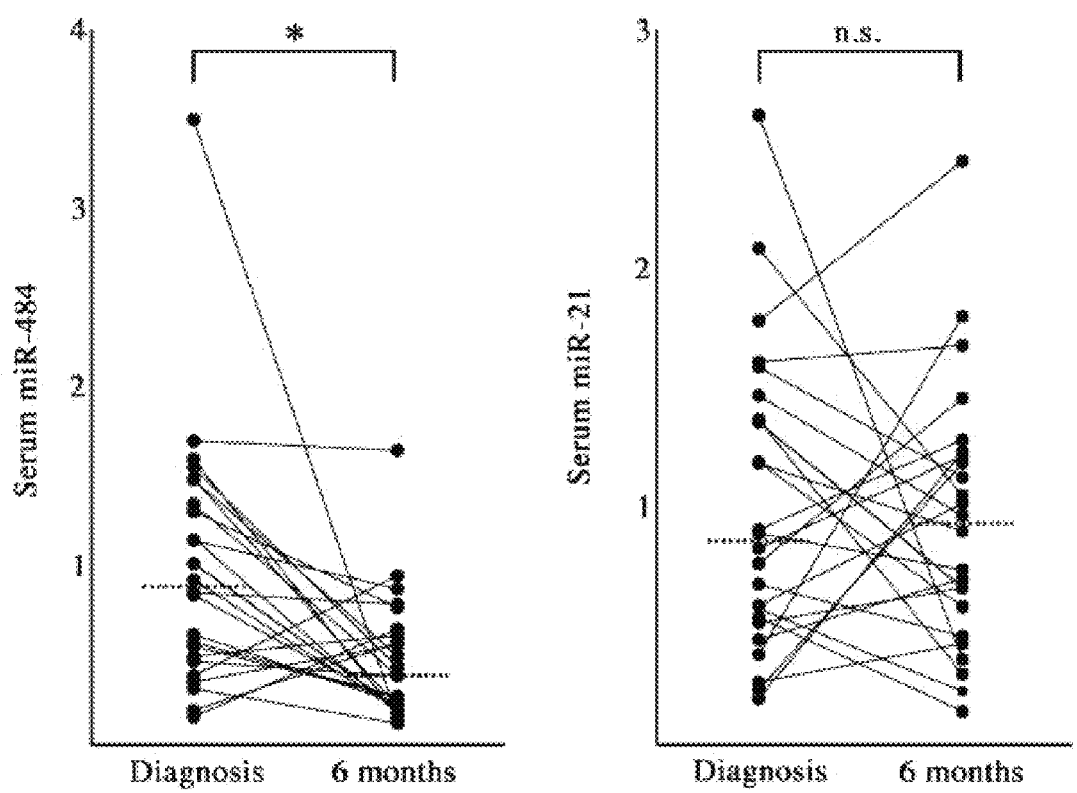
FIG. 3A-3B. Response of CD-associated circulating miRNAs following treatment. A, Dot plots of 2 CD-associated miRNAs in sera of patients with pediatric CD at diagnosis and following 6 months of treatment (n=24). Data are presented as fold-change relative to level at diagnosis. Solid lines connect data points for each patient. Dashed line=median; *P=0.003; n.s.=not significant, using the Wilcoxon matched-pairs signed rank test. B, Serum miRNA levels in patients with pediatric CD at diagnosis and following 6 months of treatment (n=24). Data are presented as fold change relative to level at diagnosis. *P=0.003 for miR-484 and P=0.037 for miR-195 using the Wilcoxon matched-pairs signed rank test. CD=Crohn disease; miRNAs=microRNAs.
Figure 3B:
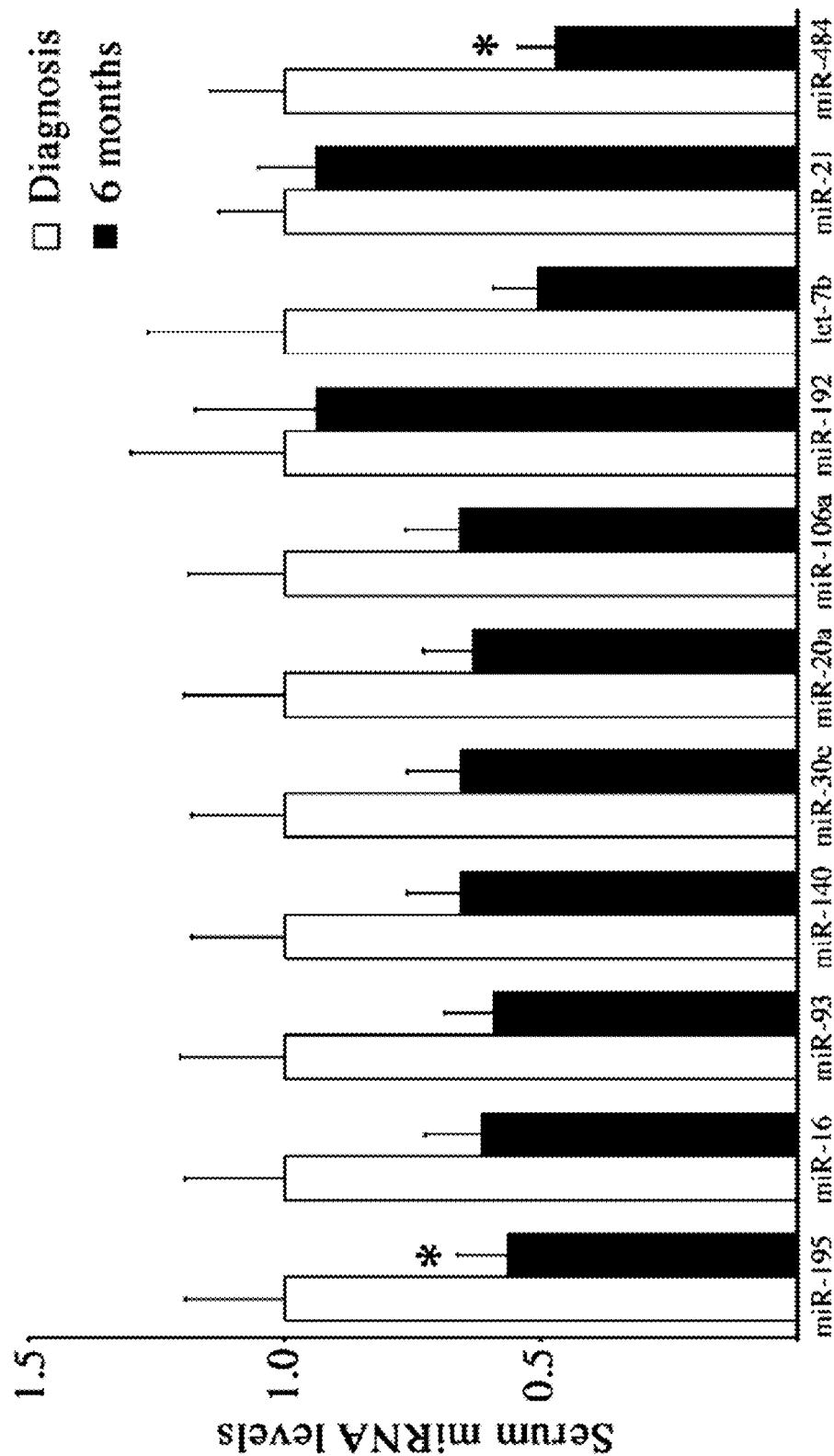

To determine whether CD-associated circulating miRNA levels change with treatment, we analyzed the sera of 24 patients with incident CD, similar to our larger cohort in terms of demographics and disease severity, at the time of diagnosis and 6 months later. Between baseline and 6 months, median PCDAI scores decreased significantly (P<0.001). At the 6-month study visit, the proportions of study subjects who had received the following medication during that interval were systemic steroids 16 (67%), methotrexate 1 (4%), 6-mercaptopurine or azathioprine 10 (42%), and infliximab 2 (8%). Significant reductions were observed in the levels of miR-484 and miR-195 (FIG. 3). All other panel miRNAs showed no significant change following treatment, although most trended downward (FIG. 3B). Changes in panel miRNA levels and PCDAI scores were not significantly correlated. These results suggest that CD-associated circulating miRNAs provide markers of response to therapeutic intervention.

TABLE 4

ROC analyses of panel miRNAs

| miRNA | AUC | 95% CI |
|---|---|---|
| miR-484 | 0.917 | 0.860-0.974 |
| miR-16 | 0.902 | 0.832-0.971 |
| miR-30e | 0.882 | 0.805-0.958 |
| miR-106a | 0.879 | 0.806-0.952 |
| miR-195 | 0.876 | 0.800-0.952 |
| miR-20a | 0.863 | 0.785-0.941 |
| let-7b | 0.860 | 0.781-0.939 |
| miR-21 | 0.853 | 0.770-0.936 |
| miR-93 | 0.852 | 0.769-0.935 |
| miR-192 | 0.834 | 0.744-0.923 |
| miR-140 | 0.821 | 0.728-0.915 |

AUC = area under the curve;
CI = confidence interval;
ROC = receiver operating characteristics.

TABLE 5

Diagnostic properties of panel miRNAs and CD-related laboratory values

| miRNA | Sensitivity, % | Specificity, % | Correctly classified, % |
|---|---|---|---|
| miR-16 | 73.91 | 100 | 84.62 |
| miR-484 | 82.61 | 84.38 | 83.33 |
| miR-30e | 73.91 | 96.88 | 83.33 |
| miR-106a | 76.09 | 90.62 | 82.05 |
| miR-195 | 69.57 | 96.88 | 80.77 |
| miR-20a | 73.91 | 87.50 | 79.49 |
| miR-21 | 76.09 | 84.38 | 79.49 |
| miR-140 | 73.91 | 87.50 | 79.49 |
| let-7b | 82.61 | 75.00 | 79.49 |
| miR-192 | 78.26 | 78.12 | 78.21 |
| miR-93 | 71.74 | 84.38 | 76.92 |

| Test | Threshold | Sensitivity, % | Specificity, % | Correctly classified, % |
|---|---|---|---|---|
| CRP | 0.9 mg/dL | 63.64 | 93.55 | 76.00 |
| ASCA IgG | 10 U/mL | 62.22 | 80.65 | 69.74 |
| ESR | 20 mm/h | 52.17 | — | — |
| Albumin | 3.5 g/dL | 41.30 | — | — |

ASCA = anti-*Saccharomyces cerevisiae* antibody;
CD = Crohn disease;
CRP = C-reactive protein;
ESR = erythrocyte sedimentation rate;
miRNAs = microRNAs.

Analysis of CD-Associated Circulating miRNAs Using Internal Reference miRNAs One obstacle to the clinical use of circulating miRNA as a biomarker derives from its acellular nature. In assays of cellular miRNAs, a variety of "housekeeping" RNA species are used commonly to correct for differences in tissue mass, RNA yield, or quality. Because no such internal controls are present for assays of circulating miRNA, in our initial assays, 2 artificial *C. elegans* miRNAs were added at the time of RNA purification and used as surrogate references (see Patients and Methods). However, it was noted in our LDA analyses that miR-150 and miR-342-3p were present at equivalent levels in patients with CD and controls. We therefore determined whether they could be used as internal reference miRNAs. The results obtained using the endogenous reference miRNAs were nearly identical to those obtained using exogenous reference miRNA. These results indicate that is possible to eliminate the use of exogenous miRNA in future studies.

Discussion

Circulating miRNAs have recently emerged as candidate biomarkers for disease, particularly cancer (36,37,39,58).

The present study is the first to demonstrate the potential of circulating miRNAs as noninvasive biomarkers of pediatric CD. An initial screen of patients with CD by microfluidic qRT-PCR array identified a significantly altered serum miRNA profile in comparison with healthy controls. These findings were subsequently validated in a much larger set of cases and controls.

All 24 miRNAs significantly altered in CD sera were elevated. The pathogenesis of IBD is a complex process involving inflammatory signaling, lymphocyte infiltration of the gut, and epithelial cell damage. Each of these may result in increases in the levels of circulating miRNA. For example, exosomes secreted in the course of inflammatory signaling may carry specific miRNAs into the circulation. The intestine is a highly vascular organ, and thus activated lymphocytes in the lamina propria may contribute to circulating miRNA. Furthermore, injury to intestinal epithelia may result in increases in epithelium-specific miRNAs in the circulation, as has been observed for tissue miRNAs in heart or liver injury (39,59). For instance, we found that circulating miR-192 is elevated in CD; miR-192 is also the most greatly expressed miRNA in intestinal epithelia (31).

In a study of intestinal miRNA levels in CD, Wu et al (35) identified several miRNAs that are upregulated; these include 4 of the miRNAs we have described (miR-16, -20a, -21, and -106a). Let-7b, miR16, and miR-21 are greatly expressed in human dendritic cells, which likely contribute to the chronic inflammation of CD (60,61). In contrast, the internal control miRNAs (miR-150 and miR-342-3p) are not detected in intestinal epithelia (62). None of the panel miRNAs are restricted to a single cell type, yet they are greatly correlated with each other, suggesting that CD may be associated with a specific circulating miRNA signature that reflects both inflammation and enteritis.

Serological testing is frequently used in the diagnosis of children with suspected IBD, although evidence suggests current markers are suboptimal as screening tools for disease in this patient population, with reported sensitivities ranging from 55% to 71% (63-65). Thus, although the diagnosis of CD ultimately must be made on histopathologic grounds, the introduction of improved noninvasive testing may help to close the gap between the onset of symptoms and the final diagnosis, allowing for earlier treatment. Conversely, a negative screening test result may help reduce unnecessary endoscopy/colonoscopy.

The serum miRNAs examined here display encouraging diagnostic utility, performing favorably in comparison with some standard serological markers. MiR-484 and let-7b each exhibited sensitivities >80%, and 3 had specificities >90% in comparison with healthy controls.

In addition, each panel miRNA was unchanged in the serum of celiac patients compared with age-, race- and sex-matched controls, suggesting that these miRNAs may be specific for IBD or CD, rather than simply indicators of intestinal inflammation in general. This finding contrasts with current IBD serological markers, which are often present in non-IBD intestinal disease. For instance, ASCA is detected in a large proportion of patients with celiac disease, whereas perinuclear anti-neutrophil cytoplasmic antibodies can also be present in celiac disease or microscopic colitis (9,12,13).

Once the diagnosis of IBD is made, the current serological markers of CD are of limited use because they correlate poorly with disease activity or outcome in both adult and pediatric patients (66,67). Studies of circulating miRNA suggest that it may be a more dynamic biomarker; for example, levels of plasma miR-1, the most abundantly expressed miRNA in the heart (68), are elevated at the time of diagnosis in acute myocardial infarction and return to normal by the time of hospital discharge (38). Likewise, miRNA released from tumor cells can significantly alter circulating miRNAs levels, which normalize following tumor resection (42,69, 70). We have found that after 6 months of treatment, serum miR-484 and miR-195 levels were significantly reduced from levels observed at the time of diagnosis. Reductions in panel miRNA levels did not significantly correlate with improved PCDAI scores. However, it remains possible that serum miRNAs accurately represent improvements at the mucosal level, as clinical scoring systems, as well as other surrogate markers, correlate poorly with mucosal healing (71,72).

In summary, this pilot study has identified a number of miRNAs significantly increased in the serum of patients with pediatric CD. These CD-associated miRNAs display encouraging clinical utility. Thus, determination of circulating miRNAs, and other laboratory, and genetic markers of CD results in composite models with improved sensitivity and specificity for IBD in general and CD in particular.

REFERENCES

1. Dotan I. Serologic markers in inflammatory bowel disease: tools for better diagnosis and disease stratification. Exp Rev Gastroenterol Hepatol 2007; 1:265-74.
2. Koutroubakis I E, Petinaki E, Mouzas I A, et al. Anti-*Saccharomyces cerevisiae* mannan antibodies and antineutrophil cytoplasmic autoantibodies in Greek patients with inflammatory bowel disease. Am J Gastroenterol 2001; 96:449-54.
3. Peeters M, Joossens S, Vermeire S, et al. Diagnostic value of anti-*Saccharomyces cerevisiae* and antineutrophil cytoplasmic autoantibodies in inflammatory bowel disease. Am J Gastroenterol 2001; 96:730-4.
4. Quinton J F, Sendid B, Reumaux D, et al. Anti-*Saccharomyces cerevisiae* mannan antibodies combined with antineutrophil cytoplasmic autoantibodies in inflammatory bowel disease: prevalence and diagnostic role. Gut 1998; 42:788-91.
5. Dubinsky M. What is the role of serological markers in IBD? Pediatric and adult data. Dig Dis 2009; 27:259-68.
6. Vermeire S, Joossens S, Peeters M, et al. Comparative study of ASCA (Anti-*Saccharomyces cerevisiae* antibody) assays in inflammatory bowel disease. Gastroenterology 2001; 120:827-33.
7. Reumaux D, Sendid B, Poulain D, et al. Serological markers in inflammatory bowel diseases. Best Pract Res Clin Gastroenterol 2003; 17:19-35.
8. Anand V, Russell A S, Tsuyuki R, et al. Perinuclear antineutrophil cytoplasmic autoantibodies and anti-*Saccharomyces cerevisiae* antibodies as serological markers are not specific in the identification of Crohn's disease and ulcerative colitis. Can J Gastroenterol 2008; 22:33-6.
9. Desplat-Jego S, Johanet C, Escande A, et al. Update on Anti-*Saccharomyces cerevisiae* antibodies, anti-nuclear associated anti-neutrophil antibodies and antibodies to exocrine pancreas detected by indirect immunofluorescence as biomarkers in chronic inflammatory bowel diseases: results of a multicenter study. World J Gastroenterol 2007; 13:2312-8.
10. Olives J P, Breton A, Hugot J P, et al. Antineutrophil cytoplasmic antibodies in children with inflammatory bowel disease: prevalence and diagnostic value. J Pediatr Gastroenterol Nutr 1997; 25:142-8.

11. Proujansky R, Fawcett P T, Gibney K M, et al. Examination of antineutrophil cytoplasmic antibodies in childhood inflammatory bowel disease. J Pediatr Gastroenterol Nutr 1993; 17:193-7.
12. Damoiseaux J G, Bouten B, Linders A M, et al. Diagnostic value of anti-*Saccharomyces cerevisiae* and antineutrophil cytoplasmic antibodies for inflammatory bowel disease: high prevalence in patients with celiac disease. J Clin Immunol 2002; 22:281-8.
13. Freeman H J. Perinuclear antineutrophil cytoplasmic antibodies in collagenous or lymphocytic colitis with or without celiac disease. Can J Gastroenterol 1997; 11:417-20.
14. Beattie R M, Walker-Smith J A, Murch S H. Indications for investigation of chronic gastrointestinal symptoms. Arch Dis Child 1995; 73:354-5.
15. Poullis A P, Zar S, Sundaram K K, et al. A new, highly sensitive assay for C-reactive protein can aid the differentiation of inflammatory bowel disorders from constipation- and diarrhoea-predominant functional bowel disorders. Eur J Gastroenterol Hepatol 2002; 14:409-12.
16. Walker T R, Land M L, Kartashov A, et al. Fecal lactoferrin is a sensitive and specific marker of disease activity in children and young adults with inflammatory bowel disease. J Pediatr Gastroenterol Nutr 2007; 44: 414-22.
17. Pfefferkorn M D, Boone J H, Nguyen J T, et al. Utility of fecal lactoferrin in identifying Crohn disease activity in children. J Pediatr Gastroenterol Nutr 2010; 51:425-8.
18. Joishy M, Davies I, Ahmed M, et al. Fecal calprotectin and lactoferrin as noninvasive markers of pediatric inflammatory bowel disease. J Pediatr Gastroenterol Nutr 2009; 48:48-54.
19. Tibble J A, Sigthorsson G, Foster R, et al. Use of surrogate markers of inflammation and Rome criteria to distinguish organic from nonorganic intestinal disease. Gastroenterology 2002; 123:450-60.
20. Wang Y, Russell I, Chen C. MicroRNA and stem cell regulation. Curr Opin Mol Ther 2009; 11:292-8.
21. Vasilatou D Papageorgiou S, Pappa V, et al. The role of microRNAs in normal and malignant hematopoiesis. Eur J Haematol 2010; 84:1-16.
22. Cai B, Pan Z, and Lu Y. The roles of microRNAs in heart diseases: a novel important regulator. Curr Med Chem 2010; 17:407-11.
23. Fineberg S K, Kosik K S, Davidson B L. MicroRNAs potentiate neural development. Neuron 2009; 64:303-9.
24. Yi R, Fuchs E. MicroRNA-mediated control in the skin. Cell Death Differ 2010; 17:229-35.
25. Iorio M V, Croce C M. MicroRNAs in cancer: small molecules with a huge impact. J Clin Oncol 2009; 27:5848-56.
26. Pandey A K, Agarwal P, Kaur K, et al. MicroRNAs in diabetes: tiny players in big disease. Cell Physiol Biochem 2009; 23:221-32.
27. Hebert S S, De Strooper B. Alterations of the microRNA network cause neurodegenerative disease. Trends Neurosci 2009; 32:199-206.
28. Latronico M V, Condorelli G. MicroRNAs and cardiac pathology. Nat Rev Cardiol 2009; 6:419-29.
29. Kato M, Arce L, Natarajan R. MicroRNAs and their role in progressive kidney diseases. Clin Am Soc Nephrol 2009; 4:1255-66.
30. Pauley K M, Cha S, Chan E K. MicroRNA in autoimmunity and autoimmune diseases. J Autoimmun 2009; 32:189-94.
31. McKenna L B, Schug J, Vourekas A, et al. MicroRNAs control intestinal epithelial differentiation, architecture, and barrier function. Gastroenterology 2010; 39:654-1664.1664 e1651.
32. Ueda T, Volinia S, Okumura H, et al. Relation between microRNA expression and progression and prognosis of gastric cancer: a micro-RNA expression analysis. Lancet Oncol 2010; 11:136-46.
33. Slaby O, Svoboda M, Michalek J, et al. MicroRNAs in colorectal cancer: translation of molecular biology into clinical application. Mol Cancer 2009; 8:102.
34. Wu F, Zikusoka M, Trindade A, et al. MicroRNAs are differentially expressed in ulcerative colitis and alter expression of macrophage inflammatory peptide-2 alpha. Gastroenterology 2008; 35:624-35. e1624.
35. Wu F, Zhang S, Dassopoulos T, et al. Identification of microRNAs associated with ileal and colonic Crohn's disease. Inflamm Bowel Dis 2010; 16:1729-38.
36. Mitchell P S, Parkin R K, Kroh E M, et al. Circulating microRNAs as stable blood-based markers for cancer detection. Proc Natl Acad Sci USA 2008; 105:10513-8.
37. Chen X, Ba Y, Ma L, et al. Characterization of microRNAs in serum: a novel class of biomarkers for diagnosis of cancer and other diseases. Cell Res 2008; 18:997-1006.
38. Ai J, Zhang R, Li Y, et al. Circulating microRNA-1 as a potential novel biomarker for acute myocardial infarction. Biochem Biophys Res Commun 2010; 391:73-7.
39. Wang G K, Zhu J Q, Zhang J T, et al. Circulating microRNA: a novel potential biomarker for early diagnosis of acute myocardial infarction in humans. Eur Heart J 2010; 31:659-66.
40. Chim S S, Shing T K, Hung E C, et al. Detection and characterization of placental microRNAs in maternal plasma. Clin Chem 2008; 54:482-90.
41. Wang K, Zhang S, Marzolf B, et al. Circulating microRNAs, potential biomarkers for drug-induced liver injury. Proc Natl Acad Sci USA 2009; 106:4402-7.
42. Tsujiura M, Ichikawa D, Komatsu S, et al. Circulating microRNAs in plasma of patients with gastric cancers. Br J Cancer 2010; 102:1174-9.
43. Kong X, Du Y, Wang G, et al. Detection of differentially expressed microRNAs in serum of pancreatic ductal adenocarcinoma patients: miR-196a could be a potential marker for poor prognosis. Dig Dis Sci 2011; 56:602-9.
44. Silva J, Garci'a V, Zaballos A, et al. Vesicle-related microRNAs in plasma of NSCLC patients and correlation with survival. Eur Respir J 2011; 37:617-23.
45. Ng E K, Chong W W, Jin H, et al. Differential expression of microRNAs in plasma of patients with colorectal cancer: a potential marker for colorectal cancer screening. Gut 2009; 58:1375-81.
46. Wu F, Guo N J, Tian H, et al. Peripheral blood microRNAs distinguish active ulcerative colitis and Crohn's disease. Inflamm Bowel Dis 2011; 17:241-50.
47. Thayu M, Denson L A, Shults J, et al. Determinants of changes in linear growth and body composition in incident pediatric Crohn's disease. Gastroenterology 2010; 139: 430-8.
48. Thayu M, Shults J, Burnham J M, et al. Gender differences in body composition deficits at diagnosis in children and adolescents with Crohn's disease. Inflamm Bowel Dis 2007; 13:1121-8.
49. Dubner S E, Shults J, Baldassano J, et al. Longitudinal assessment of bone density and structure in an incident cohort of children with Crohn's disease. Gastroenterology 2009; 136:123-30.

50. Satsangi J, Silverberg M S, Vermeire S, et al. The Montreal classification of inflammatory bowel disease: controversies, consensus, and implications. Gut 2006; 55:749-53.
51. Hyams J S, Ferry G D, Mandel F S, et al. Development and validation of a pediatric Crohn's disease activity index. J Pediatr Gastroenterol Nutr 1991; 12:439-47.
52. Suh M R, Lee Y, Kim J Y, et al. Human embryonic stem cells express a unique set of microRNAs. Dev Biol 2004; 270:488-98.
53. Pavlidis P, Noble W S. Matrix2png: a utility for visualizing matrix data. Bioinformatics 2003; 19:295-6.
54. Tusher V G, Tibshirani R, Chu G. Significance analysis of microarrays applied to the ionizing radiation response. Proc Natl Acad Sci USA 2001; 98:5116-21.
55. He L, Thomson J M, Hemann M T, et al. A microRNA polycistron as a potential human oncogene. Nature 2005; 435:828-33.
56. Kan T, Sato F, Ito T, et al. The miR-106b-25 polycistron, activated by genomic amplification, functions as an oncogene by suppressing p21 and Bim. Gastroenterology 2009; 136:1689-700.
57. Uren A G, Kool J, Matentzoglu K, et al. Large-scale mutagenesis in p19(ARF)- and p53-deficient mice identifies cancer genes and their collaborative networks. Cell 2008; 133:727-41.
58. Tan K S, Armugam A, Sepramaniam S, et al. Expression profile of MicroRNAs in young stroke patients. PLoS One 2009; 4:e7689.
59. Wang K, Zhang S, Marzolf B, et al. Circulating microRNAs, potential biomarkers for drug-induced liver injury. Proc Natl Acad Sci USA 2009; 106:4402-7.
60. Cekaite L, Clancy T, Sioud M. Increased miR-21 expression during human monocyte differentiation into DCs. Front Biosci (Elite Ed) 2010; 2:818-28.
61. Silva M A, Lopez C B, Riverin F, et al. Characterization and distribution of colonic dendritic cells in Crohn's disease. Inflamm Bowel Dis 2004; 10:504-12.
62. Davidson L A, Wang N, Shah M S, et al. n-3 Polyunsaturated fatty acids modulate carcinogen-directed non-coding microRNA signatures in rat colon. Carcinogenesis 2009; 30:2077-84.
63. Ruemmele F M, Targan S R, Levy G, et al. Diagnostic accuracy of serological assays in pediatric inflammatory bowel disease. Gastroenterology 1998; 115:822-9.
64. Hoffenberg E J, Fidanza S, Sauaia A. Serologic testing for inflammatory bowel disease. J Pediatr 1999; 134:447-52.
65. Sabery N, Bass D. Use of serologic markers as a screening tool in inflammatory bowel disease compared with elevated erythrocyte sedimentation rate and anemia. Pediatrics 2007; 19:e193-9.
66. Teml A, Kratzer V, Schneider B, et al. Anti-*Saccharomyces cerevisiae* antibodies: a stable marker for Crohn's disease during steroid and 5-aminosalicylic acid treatment. Am J Gastroenterol 2003; 98: 2226-31.
67. Desir B, Amre D K, Lu S E, et al. Utility of serum antibodies in determining clinical course in pediatric Crohn's disease. Clin Gastroenterol Hepatol 2004; 2:139-46.
68. Lagos-Quintana M, Rauhut R, Yalcin A, et al. Identification of tissue specific microRNAs from mouse. Curr Biol 2002; 12:735-9.
69. Huang Z, Huang D, Ni S, et al. Plasma microRNAs are promising novel biomarkers for early detection of colorectal cancer. Int J Cancer 2010; 127:118-26.
70. Yamamoto Y, Kosaka N, Tanaka M, et al. MicroRNA-500 as a potential diagnostic marker for hepatocellular carcinoma. Biomarkers 2009; 14: 529-38.
71. Afzal N A, Van Der Zaag-Loonen H J, Arnaud-Battandier F, et al. Improvement in quality of life of children with acute Crohn's disease does not parallel mucosal healing after treatment with exclusive enteral nutrition. Aliment Pharmacol Ther 2004; 20:167-72.
72. Efthymiou A, Viazis N, Mantzaris G, et al. Does clinical response correlate with mucosal healing in patients with Crohn's disease of the small bowel? A prospective, case-series study using wireless capsule endoscopy. Inflamm Bowel Dis 2008; 14:1542-7.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A kit for practicing a method of determining response to therapy in a human subject having Inflammatory Bowel Disease (IBD) that includes measuring in a serum sample from the subject the level of at least one differentially expressed miRNA, wherein the differentially expressed miRNA comprises miR-484 having a serum miRNA significance threshold of $p<0.05$,
said kit comprising an oligonucleotide that specifically hybridizes to at least one differentially expressed miRNA, said oligonucleotide being (i) immobilized on a solid support or (ii) detectably labeled, and one or more of a physiologically acceptable carrier, instructions for use, a container for serum, and an assay substrate;
wherein said at least one differentially expressed miRNA comprises miR-484.

2. The kit of claim 1, wherein said kit comprises an internal reference miRNA that is one or both of miR-150 and miR-342-3p.

3. The kit of claim 1, wherein the differentially expressed miRNA comprises at least two miRNA selected from the group consisting of miR-195, miR-16, miR-93, miR-140, miR-30e, miR-20a, miR-106a, miR-192, let-7b, miR-21, and miR-484.

4. The kit of claim 1, wherein the differentially expressed miRNA comprises at least five miRNA selected from the group consisting of miR-195, miR-16, miR-93, miR-140, miR-30e, miR-20a, miR-106a, miR-192, let-7b, miR-21, and miR-484.

5. The kit of claim 1, wherein the differentially expressed miRNA comprises at least ten miRNA selected from the group consisting of miR-195, miR-16, miR-93, miR-140, miR-30e, miR-20a, miR-106a, miR-192, let-7b, miR-21, and miR-484.

6. The kit of claim 1, wherein the differentially expressed miRNA comprises miR-195, miR-16, miR-93, miR-140, miR-30e, miR-20a, miR-106a, miR-192, let-7b, miR-21, and miR-484.

* * * * *